(12) United States Patent
Tischenko et al.

(10) Patent No.: US 8,571,171 B2
(45) Date of Patent: Oct. 29, 2013

(54) RECONSTRUCTING A TOMOGRAPHIC IMAGE WITH REDUCED ARTIFACTS

(75) Inventors: Oleg Tischenko, München (DE); Yuan Xu, Eugene, OR (US); Christoph Hoeschen, Hebertshausen (DE)

(73) Assignees: Helmholtz Zentrum Munchen Deutsches Forschungszentrum fur Gesundheit und Umwelt (GmbH), Neuherberg (DE); State of Oregon Acting by and through the State Board of Higher Education on Behalf of the University of Oregon, Eugene, OR (US)

( * ) Notice: Subject to any disclaimer, the term of this patent is extended or adjusted under 35 U.S.C. 154(b) by 107 days.

(21) Appl. No.: 13/132,841

(22) PCT Filed: Dec. 4, 2009

(86) PCT No.: PCT/EP2009/008681
§ 371 (c)(1),
(2), (4) Date: Jul. 14, 2011

(87) PCT Pub. No.: WO2010/063482
PCT Pub. Date: Jun. 10, 2010

(65) Prior Publication Data
US 2011/0266453 A1 Nov. 3, 2011

Related U.S. Application Data

(60) Provisional application No. 61/120,324, filed on Dec. 5, 2008.

(51) Int. Cl.
*A61B 6/00* (2006.01)
*G01T 1/161* (2006.01)
(52) U.S. Cl.
USPC .......................................... 378/4; 250/363.04
(58) Field of Classification Search
USPC ................... 378/4, 9; 250/363.01–363.04
See application file for complete search history.

(56) References Cited

U.S. PATENT DOCUMENTS 4,446,521 A * 5/1984 Inouye ............................. 378/14
4,637,040 A * 1/1987 Sohval et al. ...................... 378/9

(Continued)

FOREIGN PATENT DOCUMENTS

EP 1 371 327 12/2003
EP 1 677 253 A1 7/2006

OTHER PUBLICATIONS

Hsieh, "Adaptive streak artifact reduction in computed tomography resulting from excessive x-ray photon noise," Med. Phys. 25 (11):2139-2147 (1998).

(Continued)

*Primary Examiner* — Alexander H Taningco
(74) *Attorney, Agent, or Firm* — Klarquist Sparkman, LLP

(57) ABSTRACT

A method of reconstructing a tomographic image of a region of investigation with reduced artifacts, said method comprises the steps of (a) reconstructing a first partial image and a second partial image of the region of investigation from first and second projection profiles each of which including projection data collected at first and second different groups of parallel projection lines, resp., wherein the first and second projection profiles are provided such that streak aliasing artifacts in the first and second partial images have different spatial phases, and (b) generating the tomographic image of the region of investigation by superimposing the first and second partial images. Preferably, the first and second projection profiles are constructed such that streak aliasing artifacts in the first and second partial images have opposite spatial phases relative to each other. Furthermore, an imaging method and an imaging device for imaging a region of investigation in an object are described.

23 Claims, 5 Drawing Sheets

(56) References Cited

U.S. PATENT DOCUMENTS

| | | | | |
|---|---|---|---|---|
| 5,173,852 | A * | 12/1992 | Lonn | 378/9 |
| 5,265,142 | A * | 11/1993 | Hsieh | 378/4 |
| 5,361,291 | A * | 11/1994 | Toth et al. | 378/12 |
| 5,761,331 | A | 6/1998 | Clark, III | |
| 5,841,829 | A * | 11/1998 | Dolazza et al. | 378/4 |
| 5,987,091 | A * | 11/1999 | Miyazaki et al. | 378/15 |
| 6,233,308 | B1 * | 5/2001 | Hsieh | 378/62 |
| 6,285,732 | B1 * | 9/2001 | Hsieh | 378/4 |
| 6,404,842 | B1 * | 6/2002 | Hsieh | 378/4 |
| 6,438,195 | B1 * | 8/2002 | Hsieh | 378/4 |
| 6,459,755 | B1 * | 10/2002 | Li | 378/4 |
| 6,529,574 | B1 * | 3/2003 | Hsieh | 378/4 |
| 6,854,885 | B2 * | 2/2005 | Wischmann et al. | 378/207 |
| 2001/0043068 | A1 | 11/2001 | Lee | |
| 2003/0013953 | A1 * | 1/2003 | Mistretta | 600/425 |
| 2008/0130974 | A1 | 6/2008 | Xu et al. | |
| 2008/0175458 | A1 * | 7/2008 | Guo et al. | 382/131 |

OTHER PUBLICATIONS

Kachelrieβ et al., "Generalized multi-dimensional adaptive filtering for conventional and spiral single-slice, multi-slice, and cone-beam CT," Med. Phys. 28(4): 475-490 (2001).

Kamasak, Exact HR+ Scanner Information http://cobweb.ecn.purdue.edu/{kamasak/research/hr_plus/hrPlus.pdf> 8 pp. (retrieved 2010).

Mahmood et al., A Novel Technique for Design of Low Distortion FIR Filters, Proc. IEEE Int. Conf. on Systems Engineering, pp. 228-231 (1990).

Xu et al., Image Reconstruction by OPED Algorithm with Averaging, Numer. Algor. 45:179-193 (2007).

Xu, A New Approach to the Reconstruction of Images From Radon Projections, Advances in Applied Mathematics 36:388-420 (2006).

Written Opinion and International Search Report for International Application No. PCT/EP2009/008681 (mailed Mar. 30, 2010).

* cited by examiner

RECONSTRUCTING A TOMOGRAPHIC IMAGE WITH REDUCED ARTIFACTS

CROSS REFERENCE TO RELATED APPLICATIONS

This is the U.S. National Stage of International Application No. PCT/EP2009/008681, filed Dec. 4, 2009, which was published in English under PCT Article 21(2), which in turn claims the benefit of U.S. Provisional Application No. 61/120,324, filed Dec. 5, 2008.

ACKNOWLEDGMENT OF GOVERNMENT SUPPORT

This invention was made with government support under Grant Number DMS-0604056 awarded by the National Science Foundation. The government has certain rights in the invention.

TECHNICAL FIELD

The present invention relates to a method of reconstructing a tomographic image of a region of investigation with reduced artifacts, in particular to a reconstructing method being capable of reducing streak aliasing artifacts in a tomographic image. Furthermore, the invention relates to an imaging method for creating a tomographic image of a region of investigation, wherein the tomographic image is reconstructed in particular with reduced streak aliasing artifacts. Furthermore, the invention relates to an imaging device being adapted for implementing the reconstructing and imaging methods. Preferred applications of the invention are in the fields of computed tomography (CT) and positron emission tomography (PET) imaging.

TECHNICAL BACKGROUND OF THE INVENTION

The non-destructive investigation of objects by transmission or emission tomography imaging methods is generally known. Applications of tomography imaging, like e.g. CT imaging and PET imaging have been developed not only for medical examinations, but also in other technical fields, like e.g. materials sciences or constructions techniques.

CT imaging is based on an X-ray irradiation through a sample plane of the region of investigation with different projection directions. The collected projection data, which comprise attenuation data are subjected to a reconstructing procedure for obtaining an image function representing an image of the region of investigation.

PET imaging is based on the detection of gamma rays emitted by a positron emitting tracer substance after a positron annihilation event. The gamma radiation is detected along a plurality of projection directions (line of response direction, or coincidence line direction). Again, for obtaining the tomographic image, the projection data are subjected to a reconstructing procedure. The entirety of measured projection data, like the attenuation data of CT imaging or the coincidence data of PET imaging, represent so-called Radon data in a Radon space.

Reconstructing an image function on the basis of Radon data can be implemented with the filtered back-projection (FBP), iterative reconstruction methods or polynomial-based algorithms (OPED algorithm, US 2008 0130974 A1). The detection and the reconstructing methods may cause artifacts in the image function, like e.g. streak artifacts. Those artifacts can occur in images of objects including large contrast gradients, e.g. at sharp edges, or as a result of detector noise (noise induced artifacts). Artifacts in transmission or emission tomography may represent an essential restriction of the application of the imaging method.

As an example, artifacts may result in a wrong diagnosis or even a wrong therapeutic irradiation treatment, which is planned on the basis of CT images. In particular, due to artifact generation, the reconstruction algorithms OPED and FBP cannot be used for applications of PET imaging in nuclear medicine. Typically, PET images are reconstructed with the iterative reconstructing methods, which however have a drawback in terms of time consumption.

Artifact generation in conventional reconstructing methods represents in particular a disadvantage if different imaging techniques are to be combined. Combination of CT and PET imaging suffers from the different processing times as a result of the relatively fast OPED and FBP algorithms used for CT imaging and the slow iterative methods used for PET imaging.

Conventionally, attempts have been made for reducing imaging artifacts on the basis of physical approaches, e.g. by optimizing the scanning system or the scanning procedure. Optimization has been made for adapting the measured projection data to the requirements of both the scanning conditions and the reconstruction algorithms. As the aliasing artifacts are created as a result of an insufficient scanning resolution near the steep contrast gradient, a so-called detector offset technique has been proposed for doubling the sampling density. A further increase of the sampling density can be obtained with the "flying focus"-procedure, wherein an additional degree of freedom of the focus of the beam source of a CT device is used. These conventional techniques have disadvantages in terms of increased processing costs due to the essentially increased amount of data and complexity of the imaging device.

On the image processing side, non-linear adaptive filtering of the projection data has been proposed (see J. Hsieh: "Adaptive streak artifact reduction in computed tomography resulted from excessive x-ray photon noise" in "Med. Phys." vol. 25(11), 1998, pp. 2134-2147; and M. Kachelrieb, O. Watzke, and W. A. Kalender: "Generalized multi-dimensional adaptive filtering for conventional and spiral single-slice, multi-slice and cone-beam CT" in "Med. Phys." vol. 28(4), 2001, pp. 475-490). Parameters of the filters are locally changed in dependency on the projection data. Depending on the application, the non-linear filtering may have essential disadvantages with regard to the time-consuming image processing.

Further disadvantages of the conventional techniques are given by the fact that increasing the sampling density allows an increased resolution of the image reconstruction. Thus, the artifacts are not suppressed, but rather represented with increased resolution as well. Furthermore, practical restrictions exist with regard to the image processing approaches as a result of difficulties for defining the non-linear filters, in particular in medical applications. The main problem occurs if image details of interest are suppressed together with noisy imaging artifacts. Furthermore, the image details of interest cannot be reconstructed after a local application of a non-linear filter.

OBJECTIVE OF THE INVENTION

It is an objective of the present invention to provide an improved method of reconstructing a tomographic image avoiding disadvantages of conventional reconstructing methods. It is the particular objective of the invention to provide a reconstructing method being capable of reducing streak aliasing artifacts. Furthermore, it is an objective of the invention to provide an improved imaging method and/or imaging device avoiding disadvantages of conventional transmission or emission tomography. In particular, the imaging method and/or device are to be capable of creating tomography images with reduced artifacts.

These objectives are solved with methods and devices as defined in the independent claims. Advantageous embodiments and applications of the invention are defined in the dependent claims.

SUMMARY OF THE INVENTION

According to a first aspect of the invention, a method of reconstructing a tomographic image of a region of investigation in an object includes a separation of the projection data for providing different groups of projection profiles on the basis of which different partial images of the region of investigation are reconstructed, and a superposition of the partial images for generating the tomographic image of the region of investigation to be obtained. First and second partial images of the region of investigation are reconstructed from first and second projection profiles each of which including projection data collected at first and second different groups of parallel projection lines, resp. The first and second projection profiles (complementary projection profiles) are provided such that streak aliasing artifacts in the first and second partial images have the different spatial phases. Each (discrete) projection profile comprises projection data (projection values) corresponding to a plurality of projection lines with the same projection direction projection profiles. Projection data contributing to complementary projection profiles are called complementary projection data.

It is to be noted that the implementation of the invention is not restricted to the provision of first and second partial images on the basis of complementary projection profiles. As an alternative, three or more groups of projection profiles could be constructed, which yield three or more partial images, wherein the added harmonic components of the three or more partial images are added to zero (compensated).

According to a second aspect of the invention, an imaging method for imaging a region of investigation in an object, comprises the steps of directing a plurality of energy input beams at predetermined projection directions through the region of investigation, determining projection data measured with the plurality of energy input beams, and subjecting the projection data to a reconstructing method according to the above first aspect of the invention.

According to a third aspect of the invention, an imaging device provided for imaging a region of investigation in an object comprises a measuring device being adapted for directing a plurality of energy input beams at predetermined projection directions through the region of investigation and for determining projection data measured with the plurality of energy input beams, and a reconstruction circuit being connected with the measuring device and being adapted for reconstructing an image function with a reconstructing method the above first aspect of the invention.

The invention is based on the following findings of the inventors. Firstly, the contributions of the imaging artifacts to the image function can be described with a harmonic function (harmonic approximation). Secondly, the projection data can be provided such that the harmonic functions of the imaging artifacts in the different partial images have different spatial phases. Thus, the superposition of the partial images, which comprises e.g. an addition of the image functions of the partial images, results in a mutual compensation of the imaging artifacts contributions. Advantageously, this compensation is restricted to the imaging artifacts, while the imaging details of interest are not influenced. The tomographic image has reduced streak aliasing artifacts compared with the first and second partial images. With the superposition step, the unaltered contents of the image is reconstructed. The lost of useful image information as it may occur with conventional techniques is avoided.

Further advantages of the inventive reconstructing method are given by the facts that the artifact compensation is obtained without predetermined knowledge or preconditions on the object and that there is no essential increase of the processing costs. Furthermore, the inventive reconstructing method can be implemented with available tomography scanners.

Depending on the election of the first and second groups of parallel projection lines, the relationship of the spatial phases of the artifacts in the first and second partial images can be influenced. Thus, the above compensation of the imaging artifacts can be a partial or a complete compensation. With certain particular applications or scanning geometries, the partial compensation can be sufficient for the image reconstruction. However, according to a preferred implementation of the invention, the complete compensation of the imaging artifacts is provided. To this end, the projection data are elected such that the harmonic approximations of the imaging artifacts in the different partial images have spatial phases being opposite relative to each other. Advantageously, the harmonic approximations of the imaging artifacts are in antiphase relative to each other. By adding both contributions, the harmonic approximations cancel each other.

The superposition of the partial images results in a mutual compensation of the imaging artifacts contributions. Particular advantages in terms of a simple generation of the image of the region of investigation are obtained, if the superposition comprises an addition of the first and second partial images.

The reconstructing method of the invention can be implemented with all available transmission or emission tomography techniques. Preferably, the first and second projection data are collected with a CT device or a PET imaging device.

As a further advantage of the invention, various approaches for separating the measured projection data into different groups of projection data are available, which can be selected in dependency on e.g. the imaging technique, scanning geometry and/or requirements to the image quality.

According to a first embodiment of the invention (PET embodiment), firstly the measured projection data are resorted into projection profiles, which subsequently are separated into two groups of complementary projection profiles. As this embodiment is preferably used for reconstructing PET images, it is called PET embodiment in the following. However, this embodiment can also be implemented with other transmission or emission tomography techniques, e.g. with CT imaging.

According to a second embodiment of the invention (CT embodiment), firstly the measured projection data are separated into two groups of complementary projection data, which subsequently are resorted into projection profiles. As this embodiment is preferably used for reconstructing CT images, it is called CT embodiment in the following. Again, as there is no restriction of this embodiment to CT imaging, it can be implemented with other transmission or emission tomography techniques, e.g. PET imaging as well.

Both of the first and second embodiments can be described with reference to a scanning geometry wherein intersection points of projection lines with a circle including the region of investigation are spaced by equal angles A relative to the circle centre.

With the PET embodiment, both the intersection points of the projection lines of each of the first groups of parallel projections lines and the intersection points of the projection lines of each of the second groups of parallel projection lines being spaced by Δ, while an offset of the projection angles of the first group of projection profiles is shifted at Δ/2 relative to the angular offset of the second group of projection profiles. According, the above anti-phase relationship of the harmonic approximations of the imaging artifacts can be obtained.

With the CT embodiment, the intersection points of the projection lines of each of the first groups of parallel projection lines being spaced by 2Δ, and the intersection points of the projection lines of each of the second groups of parallel projection lines being spaced by 2Δ, wherein the intersection points of the projection lines of the first projection profiles differ from the intersection points of the projection lines of the second projection profiles by odd multiples of the angle Δ.

According to a first variant of the CT embodiment, the projection lines represent a scanning geometry such that parallel projection lines are distributed corresponding to zeros of Tschebycheff polynomials of the second kind of order [N−1]. In this case, the projection lines in each of the first projection profiles are distributed corresponding to zeros of Tschebycheff polynomials of the second kind of order [(N/2)−1], while the projection lines in each of the second projection profiles are distributed corresponding to zeros of Tschebycheff polynomials of the first kind of order [N/2].

According to a second variant of the CT embodiment, the projection lines represent a scanning geometry such that parallel projection lines are distributed corresponding to zeros of Tschebycheff polynomials of the first kind of order N. In this case, the projection lines in each of the first projection profiles are distributed corresponding to $$t_{2j} = \cos\frac{(j+1/4)\pi}{N/2},$$

j=0, 2 . . . N/2−1, while the projection lines in each of the second projection profiles are distributed corresponding to $$t_{2j+1} = \cos\frac{(j+3/4)\pi}{N/2},$$

j=0, . . . N/2−1.

Accordingly, the reconstructing steps preferably include determining image functions of the first and second partial images as sums of polynomials multiplied with the projection data of each of the first and second groups of parallel projection lines, resp., wherein the polynomials are sums of orthogonal ridge polynomials.

According to further advantageous embodiments of the invention, the reconstructing and/or the imaging method can comprise at least one of the following steps. The reconstructed image can be represented as a visualized image, in particular a single image or a series of images, to be obtained. Furthermore, image data representing the tomographic image can be stored, e.g. in a memory circuit. Furthermore, the tomographic image can be subjected to at least one further image processing step.

Further subjects of the invention are a computer program residing on a computer-readable medium, with a program code for carrying out the method according to the above first aspect of the invention and an apparatus comprising a computer-readable storage medium containing program instructions for carrying out the a method according to the above first aspect of the invention.

BRIEF DESCRIPTION OF THE DRAWINGS

Further details and advantages of the invention are described in the following with reference to the attached drawings, which show in.

PREFERRED EMBODIMENTS OF THE INVENTION

Preferred embodiments of the invention are described in the following with reference to PET and CT imaging. It is emphasized that the implementation of the invention is not restricted to these applications, but rather possible with other tomography techniques, wherein streak artifacts occur, in particular everywhere where OPED can be used as a reconstruction method, e.g. MRI. The imaging method is described in the following with particular reference to the inventive reconstructing method. Details of the imaging method and the imaging device are not described as far as they are know from conventional techniques.

Features of the Reconstructing and Imaging Methods

Figure 1:
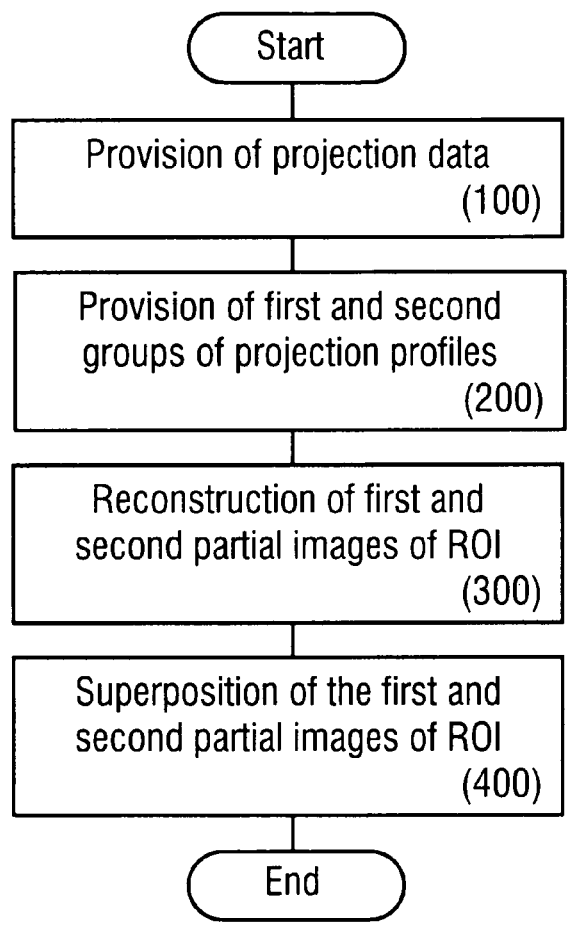
FIG. 1: a flow chart generally illustrating the steps of the inventive reconstructing method.

FIG. 1 illustrates the main steps of the reconstructing method of the invention. Firstly, the projection data to be processed are provided with step 100. As an example, step 100 may comprise supplying the projection data from a local data storage or from a distant data storage via a computer network to a reconstruction circuit being adapted for implementing the reconstructing method of the invention. As a further example, step 100 may comprise the collection of the projection data with an imaging device (e.g. FIG. 11). In the latter case, the flow chart of FIG. 1 represents an embodiment of the imaging method of the invention as well.

Subsequently, first and second groups of complementary projection profiles are constructed on the basis of the projection data (step 200). Generally, construction of the first and second projection profiles can be defined as follows.

The first and second projection profiles are provided with N detector elements such that the projection data d of the first (1) and second (2) projection profiles $\{d_{v,j}^1\}_{j=0,\ldots,N-1}^{v=0,\ldots,N-1}$ and $\{d_{v,j}^2\}_{j=0,\ldots,N-1}^{v=0,\ldots,N-1}$ fulfill $$d^1_{v,j} = R(\varphi^1_v, \cos\psi^1_j), \varphi^1_v = \frac{2\pi v}{N} \text{ or } \varphi^1_v = \frac{\pi v}{N}$$

$$d^2_{v,j} = R(\varphi^2_v, \cos\psi^2_j), \varphi^2_v = \frac{2\pi(v+\alpha)}{N} \text{ or } \varphi^2_v = \frac{\pi(v+\alpha)}{N}$$

$$\psi^1_j = (\beta + j)\frac{\pi}{N}, \psi^2_j = \left(\beta + \frac{1}{2} + j\right)\frac{\pi}{N},$$

$$0 \leq \alpha \leq 1$$

$$0 \leq \beta \leq 1$$

wherein
$0 \leq v < N$;
$0 \leq j < N$.
R means Radon transform,
φ is the projection angle (indiced in the formulaes),
ψ another angle parameter of a ray such that cos ψ is the distance between the ray and the center of the circle, and α,β are shift-parameters (fractions of the value π/N).

Details of preferred variants of step 200 are described below (see FIGS. 4, 7).

Subsequently, first and second partial images of the region of investigation are reconstructed on the basis of the first and second groups of projection profiles, respectively. The reconstruction is conducted with the OPED algorithm, i.e. image functions of the first and second partial images are calculated as sums of trigonometric polynomials multiplied with the projection data of each of the first and second groups of parallel projection lines. Details of the OPED algorithm are described in US 2008/0130974 A1, which is incorporated to the present specification by reference. As the result of the reconstruction of the first and second images (step 300), first and second image functions are provided, which are presented e.g. as tables or maps of pixel data.

Finally, the tomographic image to be obtained is generated by a superposition of the first and second images of the region of investigation (step 400). The values of the first and second image functions are added. In particular, the image function values belonging to the same spatial coordinates in the region of investigation are added element by element. After step 400, further image processing steps can be conducted, like a pattern recognition, or the reconstructed image is subjected to further data management steps like storing in a data memory or displaying with a display device.

The main effect of the inventive reconstructing method, namely the partial or complete compensation of harmonic components of the streak aliasing artifacts, is based on the appropriate election of the first and second groups of projection profiles with step 200. In the following, details of preferred variants of step 200 are described. These variants are discussed with regard to the preferred case of a complete compensation by providing projection profiles representing anti-phase components of the aliasing artifacts. It is emphasized that the implementation of the invention is not restricted to the complete artifact compensation, but is correspondingly possible with a partial compensation, if another mutual relationship of the harmonic phases of the artifacts is provided.

Figure 2:
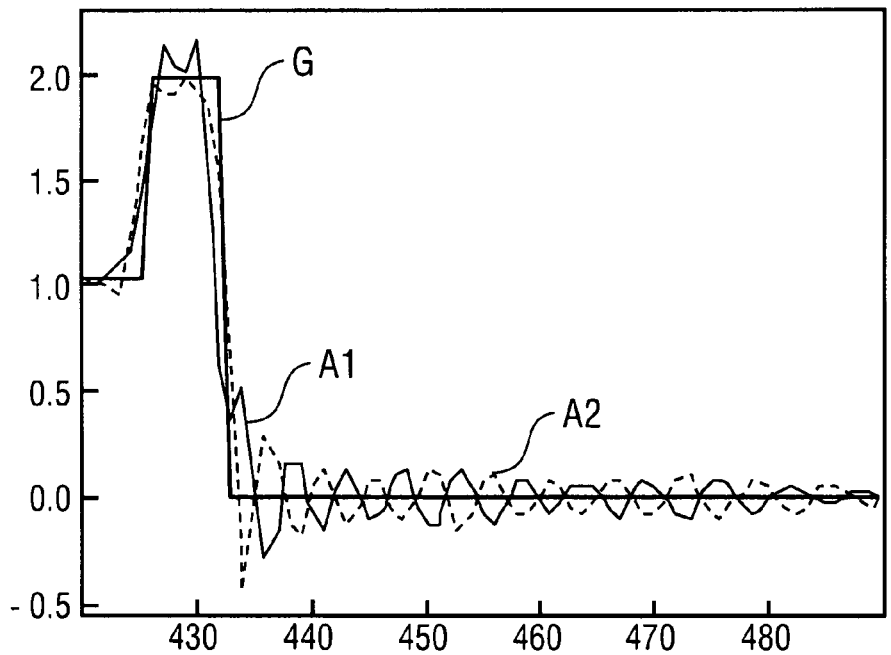
FIG. 2: a graphical illustration of the artifact compensation used in the inventive reconstructing method.

FIG. 2 illustrates the creation of aliasing artifacts at a step-like gradient G. The step-like gradient G (illustrated with a thick drawn line) is e.g. the sharp edge of an X-ray absorbing structure in the region of investigation. Image reconstruction with a first group of projection profiles (see below) yields harmonic artifact contributions A1 to the image function, which are shown with a thin drawn line. Furthermore, image reconstruction with a second group of projection profiles, which is complementary to the first group of projection profiles, yields harmonic artifact contributions A2 to the image function, which are shown with a dashed line.

The inventive separating the projection data and resorting them into complementary projection profiles means that the harmonic components of the artifact contributions have an anti-phase relationship as it can be seen in FIG. 2. Adding the partial images including the anti-phase artifact contributions yields an image function of the region of investigation wherein the artifact contributions are compensated. Only the pure image information on the real contrast structure G in the region of investigation remains in the image function.

PET Embodiment

Figure 3:
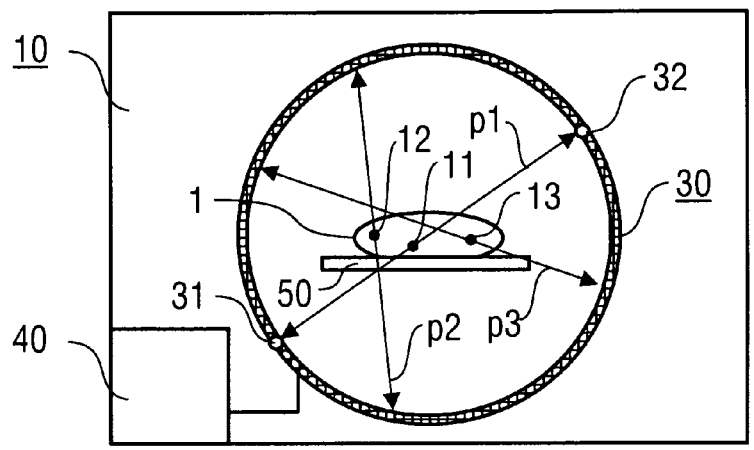
FIG. 3: a schematic illustration of the projection data collection with a PET device.

Details of the PET embodiment are described in the following with reference to FIGS. 3 to 5. FIG. 3 schematically illustrates a PET imaging device 10 with a the detector device 30. The imaging device 10 includes a reconstruction circuit 40 for reconstructing an image function with the inventive reconstructing method. The reconstruction circuit 40 is connected with the detector device 30. The detector device 30 comprises a plurality of detector elements 31, 32, which are arranged along a circle surrounding an object 1 and in particular a region of investigation thereof. The object 1 is arranged on a holding device 50, which is e.g. a carrier table. As an example, the detector device 30 comprises 300 detector elements which are arranged on the circle line with equal angular spacing. Further components like a control device, a display device etc. (not shown) are provided for as they are known per se from prior art devices.

Gamma rays emitted by a positron emitting tracer substance in the object 1 are detected with the detector elements of the detector device 30. With each positron annihilation event, e.g. at 11, 12 or 13, gamma radiation is emitted along the protection lines p1, p2 and p3, respectively. The projection data detected along all available projection lines, i.e. projection data belonging to all pairs of detector elements represent the complete Radon data used for reconstructing the PET tomography image.

For the conventional application of the OPED algorithm (US 2008 0130974 A1) the projection data are resorted for constructing projection profiles. Each projection profile represents a group of parallel projection lines. The projection data of one particular projection profile comprise the detector element signals collected with pairs of detector elements having parallel projection lines (see FIG. 5). Multiplying the projection data in the projection profiles with sums of orthogonal ridge polynomials results in an image function of the region of investigation.

According to the PET embodiment of the invention, the projection data are resorted into the projection profiles (FIG. 4, step 210) as it is known from the conventional OPED algorithm. Subsequently, the plurality of projection profiles is divided into two groups of complementary projection profiles (FIG. 4, step 220) as outlined below. On the basis of the complementary projection profiles, steps 300 and 400 of FIG. 1 are conducted.

Figure 5:
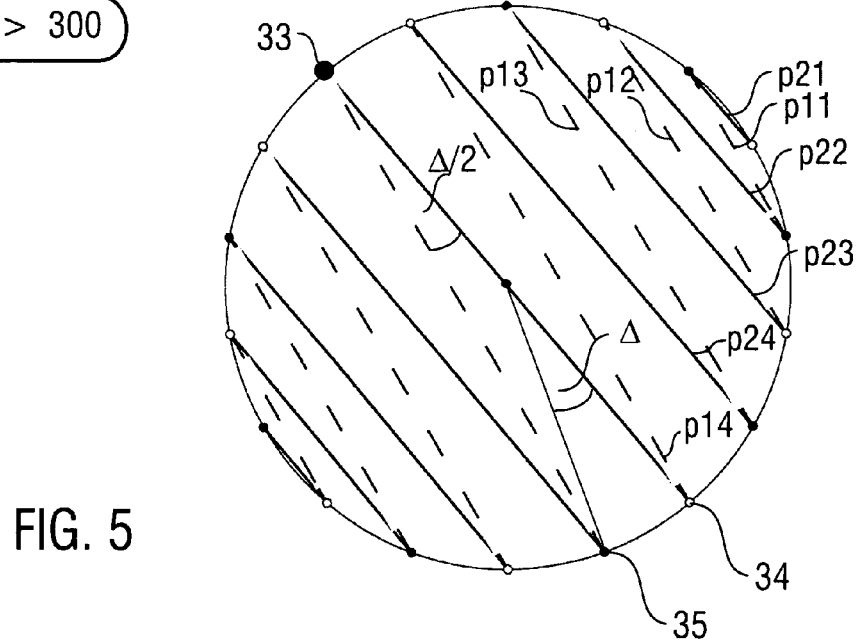
FIG. 5: an illustration of the data resorting used for the PET embodiment.

FIG. 5 illustrates the selection of complementary projection profiles with the example of 18 detector elements (e.g. 33, 34, 35) being evenly spaced on a circle line. For the sake of clarity, it is assumed that the circle line corresponds to the geometrical arrangement of the detector elements of the detector device 30 (FIG. 3). However, the corresponding consideration is possible with any other circle including the region of investigation wherein intersection points of projection lines with the circle are spaced by equal angles Δ relative to the circle centre.

The inventors have found that projection profiles having an angular offset of Δ/2 represent complementary projection profiles. Reconstructing the first and second partial images on the basis of first and second projection groups of profiles having a pairwise angular offset of $\Delta/2$ results in aliasing artefacts, which have opposite spatial phases in the partial images. Accordingly, step 220 of FIG. 4 includes the separation of the projection profiles into a first group of projection profiles and a second group of projection profiles, wherein neighbouring projection profiles having the above angular offset of $\Delta/2$ are assigned to the different groups.

Assigning the groups of parallel projections lines to the first and second projection groups of profiles can be done by the following procedure. The evenly spaced detector elements are alternately indicated as first and second (or even and odd) detector elements (shown with black and hollow circles in FIG. 5). Projection lines connecting first detector elements with first detector elements (f-f, e.g. 33-35) and second detector elements with second detector elements (s-s) are assigned to the first group of projection profiles. Projection lines connecting first detector elements with second detector elements (f-s, e.g. 33-34) or vice versa are assigned to the second group of projection profiles.

As an example, FIG. 5 illustrates the first group of parallel projection lines p11, p12, p13, p14 ... (f-f, s-s; dashed lines). The projection data of the first group of parallel projection lines provide a first projection profile. Furthermore, FIG. 5 illustrates the second group of projection lines p21, p22, p23, p24 ... (f-S, drawn lines), wherein the corresponding projection data provide a second projection profile. The intersection points (positions of the detector elements) of the first group of projection lines p11, p12, p13, p14 ... with the circle line are equally spaced by $\Delta$. The same is true with regard to the intersection points of the second group of projection lines p21, p22, p23, p24 ... with the circle line. However, the angular offset of the first and second groups of projection lines is $\Delta/2$ only as illustrated in FIG. 5.

With further projection lines (not shown in FIG. 5), further projection profiles of the first and second groups are reconstructed. The complete Radon data comprise all of the first and second groups of projection profiles.

Figure 4:
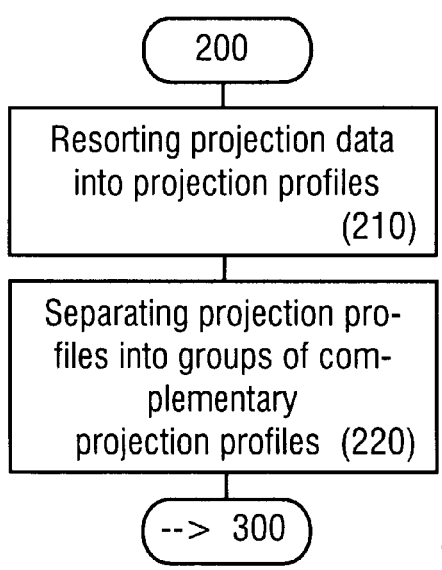
FIG. 4: a flow chart illustrating steps of the PET embodiment of the inventive reconstructing method.

The PET embodiment illustrated in FIGS. 3 to 5 can be correspondingly applied with a CT scanner geometry. In this case, the projection lines are not drawn between pairs of detector elements, but between positions of the X-ray source and the detector elements.

CT Embodiment

Figure 6:
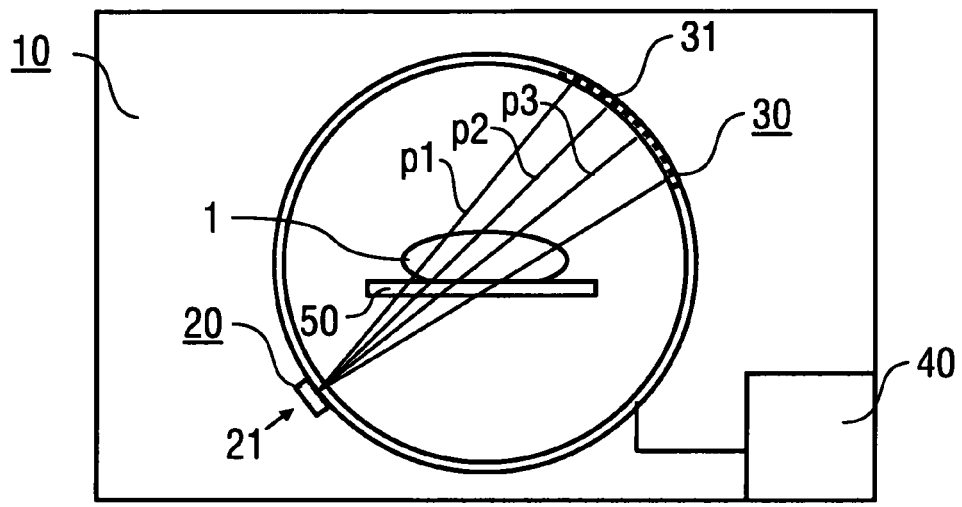
FIG. 6: a schematic illustration of the projection data collection with a CT device.
Figure 7:
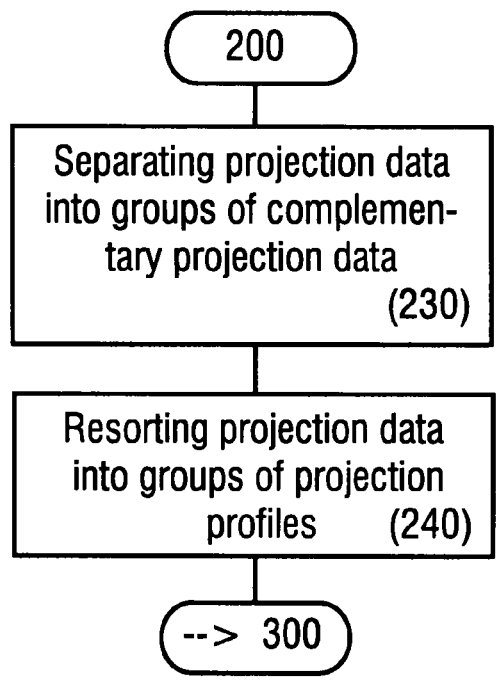
FIG. 7: a flow chart illustrating steps of the CT embodiment of the inventive reconstructing method.

An alternative approach for constructing the complementary projection profiles (CT embodiment) is illustrated in FIG. 6 to 9. In this case, firstly, the projection lines (projection data) are separated into groups of complementary projections (FIG. 7, step 230). Subsequently, two groups of projection profiles are constructed with the projection data in each of the groups of complementary projection data. The projection profiles belonging to the different groups of complementary projection data are complementary relative to each other. On the basis of the complementary projection profiles, steps 300 and 400 of FIG. 1 are conducted.

FIG. 6 schematically illustrates a CT imaging device 10 including a measuring device with a combination of an X-ray source 20 and a detector device 30. If the invention is applied in computer tomography, the imaging device 100 is structured like a current medical CT-system. The imaging device 10 includes a reconstruction circuit 40 for reconstructing an image function with the inventive reconstructing method. The reconstruction circuit 40 is connected with the measuring device. The measurement device is rotatable around the holding device 50, e.g. a carrier table with the object 1 including the region of investigation. The X-ray source 20 is adapted for emitting a fan beam comprising a continuous distribution of fan beam components. The detector device 30 comprises an array of detector elements 31 arranged along a circle segment. Each of the detector elements 31 is arranged for sensing attenuation values for certain fan beam components at each angular position of the measurement device. Further components like a control device, a display device etc. (not shown) are provided for as they are known per se from prior art devices.

With the illustrated orientation, projection lines p1, p2, p3, ... are measured. The number of projection lines depends on the spatial resolution of the detector device 30, i.e. on the sizes of the detector elements 31. As a practical example, the detector device 30 may comprises e.g. 672 detector elements (like in the Somatom Sensation Open CT Scanner, Siemens AG), which are arranged on the circle segment with equal angular spacing. Projection data (attenuation values) along each of the projection lines (e.g. p1, p2 and p3 in FIG. 6) are collected with detector elements. The positions of the detector elements are equally spaced on a circle surrounding the object 1. The angular spacing of the projection lines is $\Delta$ relative to the centre of the circle.

By way of example, FIG. 6 schematically illustrates a CT imaging device 10 with fan beam geometry. The fan beam components are resorted to the parallel beam geometry used for the OPED algorithm. Alternatively, a CT imaging device 10 with pencil beam geometry can be used.

Figure 8:
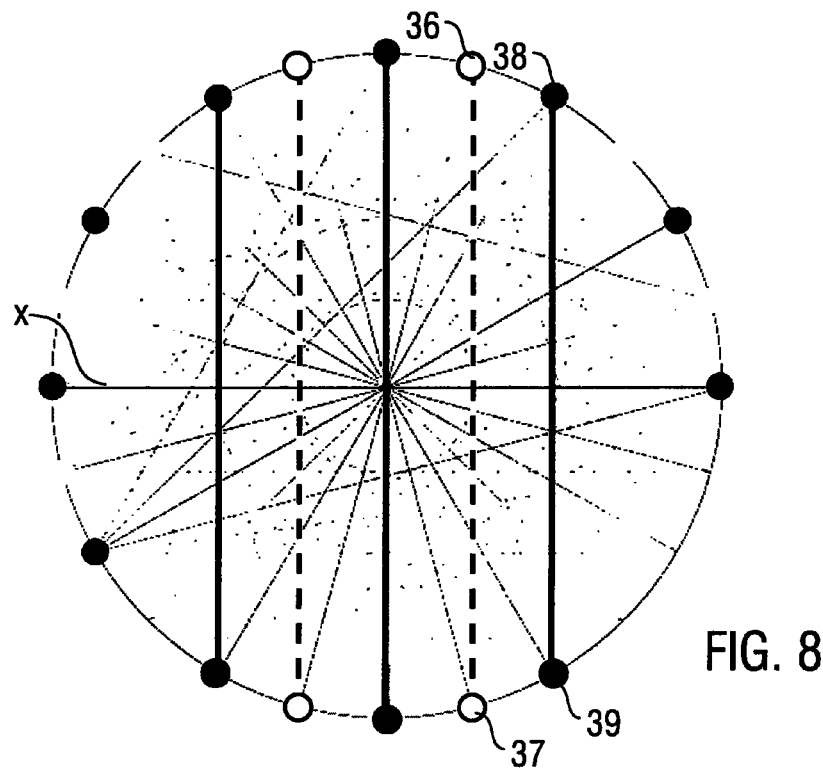
FIGS. 8 and 9: illustrations of the data resorting used for the CT embodiment.
Figure 9:
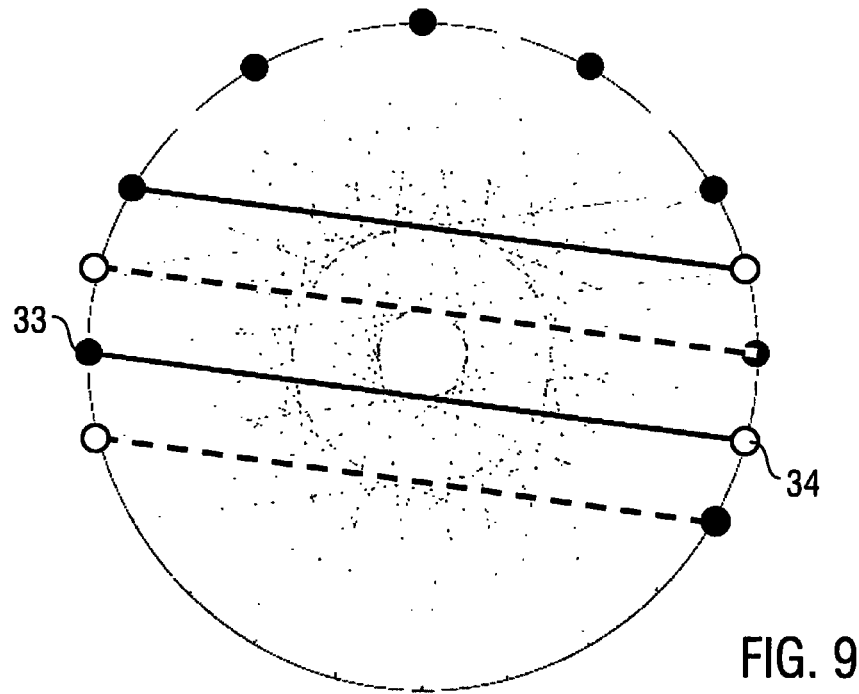

At each angular orientation, i.e. at each source device position, of the measurement device (e.g. at 21 in FIG. 8), a plurality of projection lines can be measured. In the illustrations of FIGS. 8 and 9, four and five projection lines are shown at each source device position, respectively. This small number of projection lines is shown for clarity reasons only. In practice, the number of angular positions of the source device 20 and the number of projection lines is essentially larger, e.g. 1160 source positions and 1344 projection lines per one source position.

With the CT scanning geometry, two variants of separating the projection data into groups of complementary projection data are available, which are illustrated in FIGS. 8 and 9, respectively. The separation can be done by the following procedure. In analogy with the PET embodiment, the evenly spaced positions of the source device and the detector elements are alternately indicated as first and second (or even and odd) projection positions (shown with black and hollow circles in FIGS. 8 and 9).

According to the first variant (FIG. 8), projection lines connecting first projection positions with first projection positions (f-f, e.g. 38-39) are assigned to the first group of projection data. Projection lines connecting second projection positions (s-s, e.g. 36-37) are assigned to the second group of projection data. According to the second variant (FIG. 9), projection lines connecting first projection positions with second projection positions or vice versa (f-s, e.g. 33-34) are alternating assigned to the first and second group of projection profiles.

With the first variant (FIG. 8), the projection data collected with the CT scanner are separated into two groups of complementary projection data as follows (step 230 in FIG. 7). Each second projection line within each group of parallel projection lines is assigned to the first group of projection data while the remaining projection lines are assigned to the second group of projection data. The projection lines of the first and second groups are distributed corresponding to zeros of Tschebycheff polynomials of the second and first kind. In FIG. 8, fan beam components within one group of parallel projection lines are located along line x at the positions $t_j$ $$t_j = \cos\frac{j\pi}{N},$$

j=1, ..., N-1 (in FIG. 8: N=12).

Accordingly, the projection lines within one group of parallel projection lines (f-f and s-s) are distributed corresponding to zeros of Tschebycheff polynomials of the second kind of order [N-1]. For dividing the projections into the first and second groups of projection lines, the fan beam components are separated into two groups such that the positions of the first group (drawn lines) are $t_{2j}$, j=1, 2 ... N/2-1 while the positions of the second group (dashed lines) are $t_{2j+1}$, j=0, ..., N/2-1. Accordingly, the first projections are located at $$t_{2j} = \cos\frac{j\pi}{N/2},$$

i.e. at zeros of Tschebycheff polynomials of the second kind of order N/2-1, and the second projections are located at $$t_{2j+1} = \cos\frac{(j+1/2)\pi}{N/2}$$

i.e. at zeros of Tschebycheff polynomials of the first kind of order N/2.

With the second variant (FIG. 9), an alternative geometry is implemented. In this case, parallel projection lines in each group are distributed corresponding to zeros of Tschebycheff polynomials of the first kind of order N. By assigning every second projection line to the first group of parallel projection lines and the remaining projection lines to the second group of parallel projection lines, first and second groups of projection profiles are obtained, wherein the projection lines are distributed as follows.

In FIG. 9, fan beam components within one group of parallel projection lines are located at the positions $t_j$ $$t_j = \cos\frac{(j+1/2)\pi}{N},$$

j=0, ..., N-1 (in FIG. 9: N=12).
i.e. at zeros of Tschebycheff polynomials of the first kind of order N For dividing the projections into the first and second groups of projection lines, the fan beam components are separated into two groups such that the positions of the first group (drawn lines) are $t_{2j}$, j=0, 2 ... N/2-1, while the positions of the second group (dashed lines) are $t_{2j+1}$, j=0, ..., N/2-1. Accordingly, the first projections are located at $$t_{2j} = \cos\frac{(j+1/4)\pi}{N/2},$$

j=0, 2 ... N/2-1, and the projection lines in the second projection profiles are distributed corresponding to $$t_{2j+1} = \cos\frac{(j+3/4)\pi}{N/2},$$

j=0, ... N/2-1.

The projection data (attenuation values) of the projection lines in each of the first and second groups of parallel projection lines provide first and second groups of projection profiles, which are subjected to the OPED algorithm for obtaining the partial images (step 300 in FIG. 1).

Example

Figure 10:
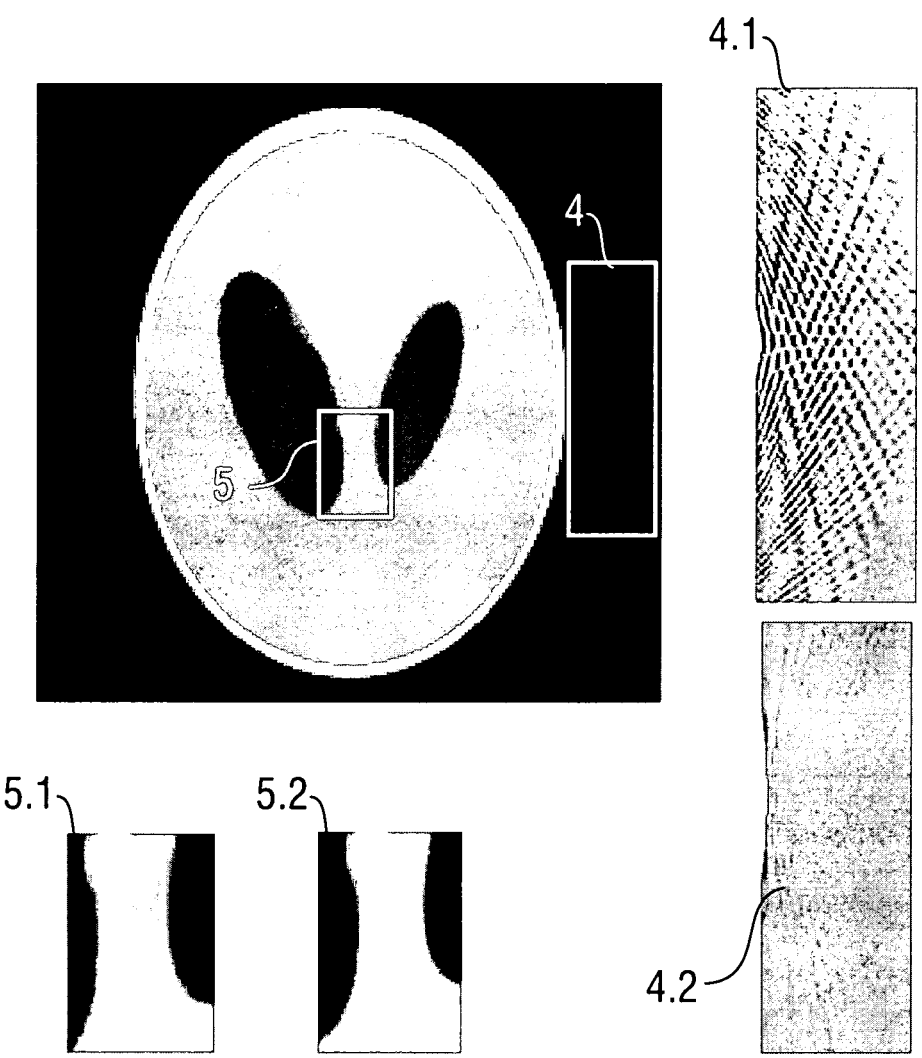
FIG. 10: an application of the artifact reduction with phantom image data.

FIG. 10 shows simulation results obtained with a Schep-Logan phantom illustrating the advantages of the invention. For printing quality reasons, a false grey value representation is used for showing the effect of invention. A first portion 4 of the phantom image in the direct neighbourhood of a steep contrast conventionally yields a reconstruction result 4.1 showing a plurality of streak aliasing artefacts. With the inventive reconstructing method, the reconstruction image 4.2 results, wherein the streak aliasing artefacts do not occur any longer. A similar result is obtained with a frame 5 showing the streak aliasing artefacts in the conventional reconstruction image 5.1. The inventive reconstruction image 5.2 is free of the artefacts.

The features of the invention disclosed in the above description, the drawings and the claims can be of significance both individually as well as in combination for the realization of the invention in its various embodiments.

The invention claimed is:

1. Method of reconstructing a tomographic image of a region of investigation with reduced artifacts, the method comprising:
   (a) reconstructing a first partial image and a second partial image of the region of investigation from first and second projection profiles each of which including projection data collected at first and second different groups of parallel projection lines, respectively, wherein the first and second projection profiles are provided such that streak aliasing artifacts in the first and second partial images have different spatial phases, and
   (b) generating the tomographic image of the region of investigation by superimposing the first and second partial images, wherein:
   the projection lines represent a scanning geometry such that parallel projection lines are distributed corresponding to zeros of Tschebycheff polynomials of the second kind of order [N-1],
   the projection lines in each of the first projection profiles are distributed corresponding to zeros of Tschebycheff polynomials of the second kind of order [(N/2)-1], and
   the projection lines in each of the second projection profiles are distributed corresponding to zeros of Tschebycheff polynomials of the first kind of order [N/2].

2. Reconstructing method according to claim 1, wherein:
   the first and second projection profiles are constructed such that streak aliasing artifacts in the first and second partial images have opposite spatial phases relative to each other.

3. Reconstructing method according to claim 1, wherein:
   the reconstructing steps include determining image functions of the first and second partial images as sums of polynomials multiplied with the projection data of each of the first and second groups of parallel projection lines, respectively, wherein the polynomials are sums of orthogonal ridge polynomials.

4. Reconstructing method according to claim 1, wherein: the step of generating the image of the region of investigation comprises adding the first and second partial images.

5. Reconstructing method according to claim 1, wherein: the first and second projection data are collected with an X-ray computer tomography (CT) device or a PET imaging device.

6. Reconstructing method according to claim 1, wherein: the projection lines represent a scanning geometry such that intersection points of the projection lines with a circle including the region of investigation are spaced by equal angles $\Delta$ relative to the circle centre, and both the intersection points of the projection lines of each of the first groups of parallel projections lines and the intersection points of the projection lines of each of the second groups of parallel projection lines being spaced by $\Delta$, while an offset of the projection angles of the first group of projection profiles is shifted at $\Delta/2$ relative to the angular offset of the second group of projection profiles.

7. Reconstructing method according to claim 1, wherein: the projection lines represent a scanning geometry such that intersection points of the projection lines with a circle including the region of investigation are spaced by equal angles $\Delta$ relative to the circle centre, the intersection points of the projection lines of each of the first groups of parallel projection lines being spaced by $2\Delta$, the intersection points of the projection lines of each of the second groups of parallel projection lines being spaced by $2\Delta$, and the intersection points of the projection lines of the first projection profiles differ from the intersection points of the projection lines of the second projection profiles by odd multiples of the angle $\Delta$.

8. Reconstructing method according to claim 1, wherein: the first and second projection profiles are provided such that the projection data d of the first and second projection profiles $\{d_{v,j}^1\}_{j=0,\ldots,N-1}^{v=0,\ldots,N-1}$ and $\{d_{v,j}^2\}_{j=0,\ldots,N-1}^{v=0,\ldots,N-1}$ fulfill $$d_{v,j}^1 = R(\varphi_v^1, \cos\psi_j^1), \varphi_v^1 = \frac{2\pi v}{N} \text{ or } \varphi_v^1 = \frac{\pi v}{N}$$

$$d_{v,j}^2 = R(\varphi_v^2, \cos\psi_j^2), \varphi_v^2 = \frac{2\pi(v+\alpha)}{N} \text{ or } \varphi_v^2 = \frac{\pi(v+\alpha)}{N}$$

$$\psi_j^1 = (\beta+j)\frac{\pi}{N}, \psi_j^2 = \left(\beta+\frac{1}{2}+j\right)\frac{\pi}{N},$$

$$0 \le \alpha \le 1$$

$$0 \le \beta \le 1$$

wherein R is the Radon transformation.

9. Reconstructing method according to claim 1, further comprising at least one of the steps of:
representing an approximation of the tomographic image as a visualized image to be obtained,
storing image data representing the tomographic image, and
subjecting the tomographic image to an image processing step.

10. Method of reconstructing a tomographic image of a region of investigation with reduced artifacts, the method comprising:
(a) reconstructing a first partial image and a second partial image of the region of investigation from first and second projection profiles each of which including projection data collected at first and second different groups of parallel projection lines, respectively, wherein the first and second projection profiles are provided such that streak aliasing artifacts in the first and second partial images have different spatial phases, and
(b) generating the tomographic image of the region of investigation by superimposing the first and second partial images, wherein:
the projection lines represent a scanning geometry such that parallel projection lines are distributed corresponding to zeros of Tschebycheff polynomials of the first kind of order N,
the projection lines in each of the first projection profiles are distributed corresponding to $$t_{2j} = \cos\frac{(j+1/4)\pi}{N/2},$$

$j=0, 2, \ldots N/2-1$, and
the projection lines in each of the second projection profiles are distributed corresponding to $$t_{2j+1} = \cos\frac{(j+3/4)\pi}{N/2},$$

$j=0, \ldots N/2-1$.

11. Reconstructing method according to claim 10, wherein:
the first and second projection profiles are constructed such that streak aliasing artifacts in the first and second partial images have opposite spatial phases relative to each other.

12. Reconstructing method according to claim 10, wherein:
the reconstructing steps include determining image functions of the first and second partial images as sums of polynomials multiplied with the projection data of each of the first and second groups of parallel projection lines, respectively, wherein the polynomials are sums of orthogonal ridge polynomials.

13. Reconstructing method according to claim 10, wherein:
the step of generating the image of the region of investigation comprises adding the first and second partial images.

14. Reconstructing method according to claim 10, wherein:
the projection lines represent a scanning geometry such that intersection points of the projection lines with a circle including the region of investigation are spaced by equal angles $\Delta$ relative to the circle centre,
the intersection points of the projection lines of each of the first groups of parallel projection lines being spaced by $2\Delta$,
the intersection points of the projection lines of each of the second groups of parallel projection lines being spaced by $2\Delta$, and the intersection points of the projection lines of the first projection profiles differ from the intersection points of the projection lines of the second projection profiles by odd multiples of the angle $\Delta$.

15. Reconstructing method according to claim 10, wherein:

the first and second projection profiles are provided such that the projection data d of the first and second projection profiles $\{d_{v,j}^1\}_{j=0,\ldots,N-1}^{v=0,\ldots,N-1}$ and $\{d_{v,j}^2\}_{j=0,\ldots,N-1}^{v=0,\ldots,N-1}$ fulfill $$d_{v,j}^1 = R(\varphi_v^1, \cos\psi_j^1), \varphi_v^1 = \frac{2\pi v}{N} \text{ or } \varphi_v^1 = \frac{\pi v}{N}$$

$$d_{v,j}^2 = R(\varphi_v^2, \cos\psi_j^2), \varphi_v^2 = \frac{2\pi(v+\alpha)}{N} \text{ or } \varphi_v^2 = \frac{\pi(v+\alpha)}{N}$$

$$\psi_j^1 = (\beta + j)\frac{\pi}{N}, \psi_j^2 = \left(\beta + \frac{1}{2} + j\right)\frac{\pi}{N},$$

$$0 \le \alpha \le 1$$

$$0 \le \beta \le 1$$

wherein R is the Radon transformation.

16. Reconstructing method according to claim 10, further comprising at least one of the steps of:

representing an approximation of the tomographic image as a visualized image to be obtained, storing image data representing the tomographic image, and subjecting the tomographic image to an image processing step.

17. Imaging method for imaging a region of investigation in an object, comprising:

directing a plurality of energy input beams at predetermined projection directions through the region of investigation, determining projection data measured with the plurality of energy input beams, and subjecting the projection data to a reconstructing method according to claim 1.

18. Imaging device for imaging a region of investigation in an object, the imaging device comprising:

a measuring device being adapted for directing a plurality of energy input beams at predetermined projection directions through the region of investigation, and for determining projection data measured with the plurality of energy input beams, and a reconstruction circuit, connected with the measuring device, for reconstructing an image function, wherein the reconstruction circuit is configured to reconstruct a tomographic image of the region of investigation with reduced artifacts by:

(a) reconstructing a first partial image and a second partial image of the region of investigation from first and second projection profiles each of which including projection data collected at first and second different groups of parallel projection lines, respectively, wherein the first and second projection profiles are provided such that streak aliasing artifacts in the first and second partial images have different spatial phases, and (b) generating the tomographic image of the region of investigation by superimposing the first and second partial images, wherein:

the projection lines represent a scanning geometry such that parallel projection lines are distributed corresponding to zeros of Tschebycheff polynomials of the second kind of order [N−1], the projection lines in each of the first projection profiles are distributed corresponding to zeros of Tschebycheff polynomials of the second kind of order [(N/2)−1], and the projection lines in each of the second projection profiles are distributed corresponding to zeros of Tschebycheff polynomials of the first kind of order [N/2].

19. Computer program residing on at least one non-transitory computer-readable medium, comprising computer-executable instructions for performing a method for reconstructing a tomographic image of a region of investigation with reduced artifacts, the method comprising:

(a) reconstructing a first partial image and a second partial image of the region of investigation from first and second projection profiles each of which including projection data collected at first and second different groups of parallel projection lines, respectively, wherein the first and second projection profiles are provided such that streak aliasing artifacts in the first and second partial images have different spatial phases, and (b) generating the tomographic image of the region of investigation by superimposing the first and second partial images, wherein:

the projection lines represent a scanning geometry such that parallel projection lines are distributed corresponding to zeros of Tschebycheff polynomials of the second kind of order [N−1], the projection lines in each of the first projection profiles are distributed corresponding to zeros of Tschebycheff polynomials of the second kind of order [(N/2)−1], and the projection lines in each of the second projection profiles are distributed corresponding to zeros of Tschebycheff polynomials of the first kind of order [N/2].

20. Apparatus comprising at least one non-transitory computer-readable storage medium, comprising computer-executable instructions for performing a method for reconstructing a tomographic image of a region of investigation with reduced artifacts, the method comprising:

(a) reconstructing a first partial image and a second partial image of the region of investigation from first and second projection profiles each of which including projection data collected at first and second different groups of parallel projection lines, respectively, wherein the first and second projection profiles are provided such that streak aliasing artifacts in the first and second partial images have different spatial phases, and (b) generating the tomographic image of the region of investigation by superimposing the first and second partial images, wherein:

the projection lines represent a scanning geometry such that parallel projection lines are distributed corresponding to zeros of Tschebycheff polynomials of the second kind of order [N−1], the projection lines in each of the first projection profiles are distributed corresponding to zeros of Tschebycheff polynomials of the second kind of order [(N/2)−1], and the projection lines in each of the second projection profiles are distributed corresponding to zeros of Tschebycheff polynomials of the first kind of order [N/2].

21. Imaging method for imaging a region of investigation in an object, comprising:

directing a plurality of energy input beams at predetermined projection directions through the region of investigation, determining projection data measured with the plurality of energy input beams, and subjecting the projection data to a reconstructing method according to claim 10.

22. Imaging device for imaging a region of investigation in an object, the imaging device comprising:

a measuring device being adapted for directing a plurality of energy input beams at predetermined projection directions through the region of investigation, and for determining projection data measured with the plurality of energy input beams, and a reconstruction circuit, connected with the measuring device, for reconstructing an image function, wherein the reconstruction circuit is configured to reconstruct a tomographic image of the region of investigation with reduced artifacts by:

(a) reconstructing a first partial image and a second partial image of the region of investigation from first and second projection profiles each of which including projection data collected at first and second different groups of parallel projection lines, respectively, wherein the first and second projection profiles are provided such that streak aliasing artifacts in the first and second partial images have different spatial phases, and (b) generating the tomographic image of the region of investigation by superimposing the first and second partial images, wherein:

the projection lines represent a scanning geometry such that parallel projection lines are distributed corresponding to zeros of Tschebycheff polynomials of the first kind of order N, the projection lines in each of the first projection profiles are distributed corresponding to $$t_{2j} = \cos\frac{(j+1/4)\pi}{N/2},$$

j=0, 2, ... N/2−1, and the projection lines in each of the second projection profiles are distributed corresponding to $$t_{2j+1} = \cos\frac{(j+3/4)\pi}{N/2},$$

j=0, ... N/2−1; and wherein the reconstruction circuit is connected with the measuring device.

23. At least one non-transitory computer-readable medium, comprising computer-executable instructions for performing a method for reconstructing a tomographic image of a region of investigation with reduced artifacts, the method comprising:

(a) reconstructing a first partial image and a second partial image of the region of investigation from first and second projection profiles each of which including projection data collected at first and second different groups of parallel projection lines, respectively, wherein the first and second projection profiles are provided such that streak aliasing artifacts in the first and second partial images have different spatial phases, and (b) generating the tomographic image of the region of investigation by superimposing the first and second partial images, wherein:

the projection lines represent a scanning geometry such that parallel projection lines are distributed corresponding to zeros of Tschebycheff polynomials of the first kind of order N, the projection lines in each of the first projection profiles are distributed corresponding to $$t_{2j} = \cos\frac{(j+1/4)\pi}{N/2},$$

j=0, 2, ... N/2−1, and the projection lines in each of the second projection profiles are distributed corresponding to $$t_{2j+1} = \cos\frac{(j+3/4)\pi}{N/2},$$

j=0, ... N/2−1.

* * * * *